United States Patent [19]

Shibasaki et al.

[11] Patent Number: 4,879,281

[45] Date of Patent: Nov. 7, 1989

[54] ARTIFICIAL SALIVA COMPOSITION

[75] Inventors: Ken-ichiro Shibasaki, Chiba; Hiroshi Itoi, Kamagaya; Shouichi Ohkubo, Tokyo; Hiroshi Sano, Narashino, all of Japan

[73] Assignee: Lion Corporation, Tokyo, Japan

[21] Appl. No.: 27,388

[22] Filed: Mar. 18, 1987

[30] Foreign Application Priority Data

Mar. 24, 1986 [JP] Japan .................................. 61-66135

[51] Int. Cl.$^4$ .............................................. A61K 31/70
[52] U.S. Cl. ...................................................... 514/55
[58] Field of Search ............................ 514/55; 536/20

[56] References Cited

U.S. PATENT DOCUMENTS

| | | | |
|---|---|---|---|
| 4,027,068 | 5/1977 | Saad | 536/20 |
| 4,223,023 | 9/1980 | Furda | 514/55 |
| 4,363,801 | 12/1982 | Nagyvary | 514/55 |
| 4,452,785 | 6/1984 | Malette et al. | 514/55 |
| 4,512,968 | 4/1985 | Komiyama et al. | 514/55 |

FOREIGN PATENT DOCUMENTS

| | | |
|---|---|---|
| 52-108014 | 9/1977 | Japan . |
| 53-47479 | 4/1978 | Japan . |
| 59-7116 | 1/1984 | Japan . |
| 59-27818 | 2/1984 | Japan . |
| 60-186504 | 9/1985 | Japan . |

*Primary Examiner*—Johnnie R. Brown
*Assistant Examiner*—Elli Peselev
*Attorney, Agent, or Firm*—Armstrong, Nikaido, Marmelstein, Kubovcik & Murray

[57] ABSTRACT

An artificial saliva composition comprising at least one buffering compound selected from the group consisting of chitins and chitosans in a medium. The artificial saliva composition has a pH buffering capacity similar to natural saliva and an excellent caries preventing effect.

5 Claims, 1 Drawing Sheet

ARTIFICIAL SALIVA COMPOSITION

BACKGROUND OF THE INVENTION

1. Field of the Invention

The present invention relates to an artificial saliva composition suitable for application to hydrodipsia (or thirst) caused by sialadenitis. More specifically, it relates to an artificial saliva composition having a pH buffering capability similar to natural saliva and a high caries preventing effect.

2. Description of the Related Art

Known in the art as an artificial saliva composition for application to, for example, hydrodipsia caused by sialadenitis, are aqueous solutions containing inorganic cations and anions contained in natural saliva, phosphate buffers for pH adjustment, and a thickening agent such as carboxymethyl cellulose. Various attempts have been made to improve the conventional artificial saliva compositions. For example, Japanese Unexamined Patent Publication (i.e., Kokai) No. 52-108014 (or JP-A-52-108014) proposes artificial saliva compositions further containing digestive enzymes, hormones, and bactericides in the above-mentioned conventional artificial saliva compositions. Japanese Kokai Nos. 59-7116 and 59-27818 propose artificial saliva compositions having a very low viscosity change over a wide pH range and containing, as a thickening agent, hydroxypropyl cellulose, methyl cellulose, or hydroxypropylmethyl cellulose.

Artificial saliva compositions are used as substituents for natural saliva and, therefore, should preferably possess all the functions of natural saliva. Of these functions of natural saliva, the pH buffering capacity is the most important, since the generation of caries can be inhibited by this pH buffering capacity. That is, caries occurs because enamels (i.e., hydroxyapatite) that form the surface layer of teeth, are subjected to decalcification by acids produced by microorganisms such as *Streptococcus mutans*. This decalcification is accelerated when the pH in the oral cavity becomes less than 5.5. Accordingly, to prevent the generation of caries, preferably the pH in the oral cavity is within the range of 5.5 or more. Natural saliva has a special buffering action, and the pH in the oral cavity is always maintained at a pH of 5.5 or more, whereby the generation of caries is inhibited.

However, the conventional artificial saliva compositions all have low pH buffering capacities and do not possess the special buffering actions of natural saliva.

Therefore, when conventional artificial saliva compositions are used, the pH in the oral cavity is greatly changed, and in particular, is decreased to a pH of less than 5.5 due to the presence of acids produced by microorganisms. As a result, the surface enamel of the teeth may be subjected to decalcification and caries may be generated.

SUMMARY OF THE INVENTION

Accordingly, the objects of the present invention are to eliminate the above-mentioned disadvantages of the prior art and to provide an artificial saliva composition having a pH buffering capacity similar to that of natural saliva and an excellent caries preventing effect.

Other objects and advantages of the present invention will be apparent from the following description.

In accordance with the present invention, there is provided an artificial saliva composition comprising at least one buffering compound selected from the group consisting of chitins and chitosans in a medium.

BRIEF DESCRIPTION OF THE DRAWINGS

The present invention will be better understood from the description set forth below with reference to the accompanying drawing of FIG. 1, which shows pH buffering capacity curves obtained in Example 1.

DESCRIPTION OF THE PREFERRED EMBODIMENT

Figure 1:
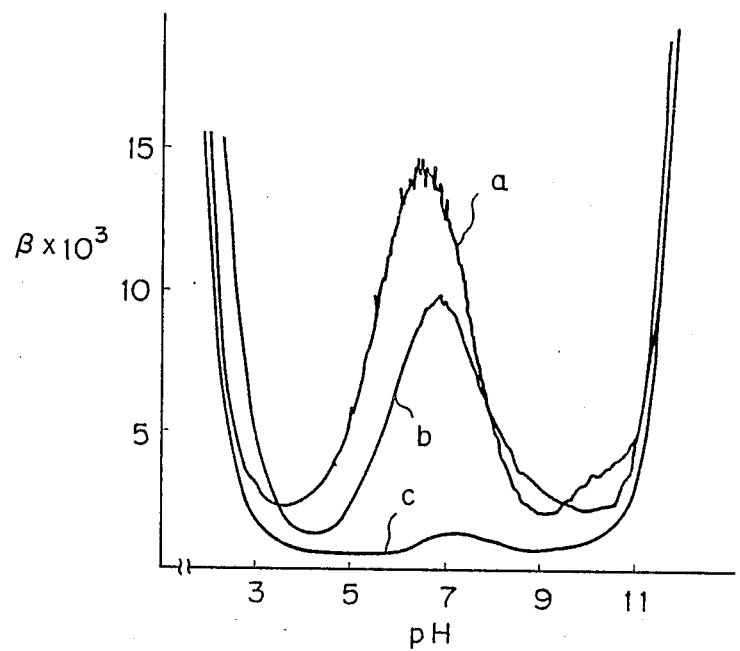

As mentioned above, according to the present invention, one or more compounds selected from chitins and chitosans are formulated into artificial saliva compositions to achieve the above-mentioned objects of the present invention. The present inventors have found that, when chitins and chitosans having buffering capacities based on the free amino residues therein are formulated into artificial saliva compositions they exhibit buffering actions similar to natural saliva, in that the pH change in the oral cavity, especially the remarkable decrease in the pH, can be prevented when such artificial saliva compositions are applied. Accordingly, when chitins and chitosans are formulated into artificial saliva compositions, desirable buffering capacities similar to those of natural saliva can be provided and, therefore, the occurrence of a pH condition of less than 5.5 in the oral cavity, under which decalcification of the tooth enamel may occur, can be effectively inhibited to prevent the generation of caries.

The artificial saliva composition according to the present invention contains one or more compounds selected from the group consisting of chitins and chitosans, for example, at a concentration of 0.01% to 5% by weight, more preferably 0.1% to 2% by weight. This artificial saliva composition can be prepared as an aqueous solution, which can be applied directly (i.e., undiluted) or after dilution with water. Alternatively, the present artificial saliva composition can be prepared in the form of, for example, powders, granules, grains, tablets, liquids, or concentrates, which can be applied after being dissolved or suspended in water or an aqueous medium.

The term "chitins" as used herein means chitin and its derivatives, and the term "chitosans" as used herein means chitosan and its derivatives.

Chitin is a compound obtained by multi-bonding N-acetylated D-glucosamine having the following general formula (A) at the $\beta$-1,4 position.

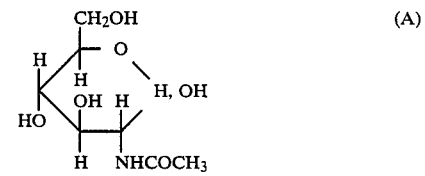

Chitin is widely distributed in natural forms, for example, as an organic structural substance in arthropods, mollusks, and the like as well as in spores and hypha of fungi. For example, chitin can be produced in the form of white flakes from shells (or cursts) of crabs, prawns (or shrimps), or krills. That is, these shells are crushed, followed by treating with hydrochloric acid, thereby removing the calcium carbonate.

The resultant mixture is then treated with sodium hydroxide to remove the proteins and other contaminants or impurities therefrom, followed by water washing and drying; thus producing the desired chitin flakes.

On the other hand, chitosan is a deacetylated product of chitin and can be readily prepared from chitin in the form of white flakes by, for example, treating chitin with an alkali. Chitosan is commercially available from, for example, Kyowa Yushi Kogyo K.K. (Japan), under the tradename of "Flonac-N".

The derivatives of chitin and chitosan usable in the present invention include the following water-soluble compounds derived from chitin and chitosan.

(1) Water-soluble oligomers of chitin or chitosan obtained by depolymerizing chitin or chitosan to the low molecules (Note: provided that they have a polymerization degree of the glucosamine unit of greater than 1).

These oligomers may be prepared by conventional depolymerization methods, for example, nitrite decomposition, formic acid decomposition, chlorine decomposition (see Japanese Kokai No. 60-186504), and enzyme or microorganism decomposition.

(2) Water-soluble partially deacetylated chitins preferably having a degree of deacetylation of 40 to 60%.

These derivatives can be prepared by controlling the degree of deacetylation of chitin by the method disclosed in, for example, Japanese Kokai No. 53-47479.

(3) Salts of organic or inorganic acids of chitosan.

Typical examples of the organic acids are acetic acid, malic acid, citric acid, and ascorbic acid and typical examples of the inorganic acids are hydrochloric acid, sulfuric acid, and phosphoric acid.

(4) Water-soluble derivatives obtained by introducing hydrophilic groups into chitin or chitosan.

Examples of these derivatives are as follows:

(i) Polyoxyethylene.polyoxypropylene chitin or chitosan:

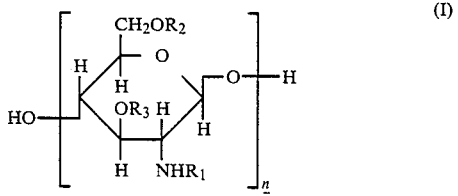

(I)

wherein
n: >1, preferably 3-100
$R_1$: —H, —COCH$_3$ or $+EO+_{l1}+PO-_{m1}$H wherein l1=0-5, m1=0-5, l1+m1≠0
$R_2$: —H or $+EO+_{l2}+PO+_{m2}$H wherein l2=0-5, m2=0-5, l2+m2≠0
$R_3$: —H or $+EO+_{l3}+PO+_{m3}$H l3=0-5, m3=0-5, l3+m3≠0

In the above-definition, EO represents an oxyethylene chain and PO represents an oxypropylene chain. Furthermore, the bonding order of EO and PO may be randomized. For example, PO may be first bonded to the D-glucosamine skeleton and then EO may be bonded, or EO and PO may be bonded to the D-glucosamine skeleton at random. In each bonded D-glucosamine skeleton, $R_1$, $R_2$, $R_3$, $m_1$, $m_2$, $m_3$, $l_1$, $l_2$, and $l_3$ may be the same or different.

The polyoxyethylene.polyoxypropylene glycol chitin or chitosan can be prepared by reacting alkali chitin or chitosan with chlorohydroxy ethylene, chlorohydroxy propylene, ethylene oxide, and/or propylene oxide under an ambient temperature and ambient pressure, or at a temperature of 50° C. to 60° C. and a pressure of 1 to 5 kg/cm²G.

(ii) Carboxymethyl chitin or chitosan

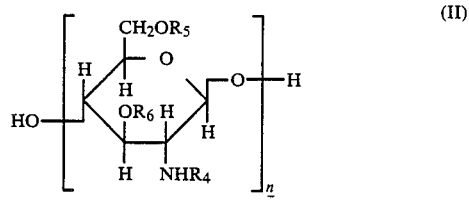

(II)

wherein
n: >1, preferably 3-100
$R_4$: —H or —COCH$_3$
$R_5$: —H, CH$_2$COOH, —CH$_2$COONa, —CH$_2$COOK or CH$_2$COONH$_4$
$R_6$: —H, CH$_2$COOH, —CH$_2$COONa, —CH$_2$COOK or CH$_2$COONH$_4$ In the above definition, $R_5$ and $R_6$ are not —H at the same time and $R_4$, $R_5$, and $R_6$ may be the same or different in each bonded D-glucosamine skeleton.

The carboxymethyl chitin or chitosan can be prepared by reacting alkali chitin or chitosan with monochloroacetic acid under an ambient temperature and ambient pressure.

(iii) Phosphorated chitin or chitosan

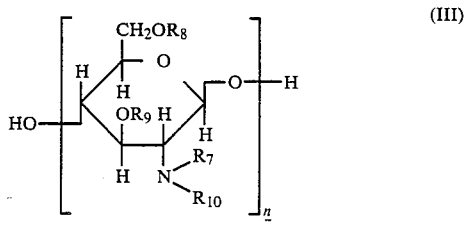

(III)

Wherein n: >1, preferably 3-100, $$R_7: -H, -COCH_2 \text{ or } -\overset{OM_1}{\underset{OM_2}{P}}=O$$

wherein $M_1$ and $M_2$ is —H, Na, K or —NH$_4$, $$R_8: -H \text{ or } -\overset{OM_3}{\underset{OM_4}{P}}=O$$

wherein $M_3$ and $M_4$ is —H, Na, K or —NH$_4$, $$R_9: -H \text{ or } -\overset{OM_5}{\underset{OM_6}{P}}=O$$

wherein $M_5$ and $M_6$ is —H, Na, K or —NH$_4$,
provided that $R_8$ and $R_9$ are not —H at the same time, $$R_{10}: -H, COCH_3 \text{ or } -\overset{OM_7}{\underset{OM_8}{P}}=O$$

wherein $M_7$ and $M_8$ is —H, Na, K or —NH$_4$

Furthermore, $R_7$, $R_8$, $R_9$, and $R_{10}$ are the same or different, respectively, in the each bonded D-glucosamine skeleton.

The phosphorated chitin or chitosan can be prepared by reacting diphosphorus pentaoxide to chitin or chitosan dissolved or suspended in methanesulfonic acid, while coolng. This method was disclosed in, for example, Norio Nishi, Preparatory Papers II, page 570, at the 48th Autumn Annual Convention Lecture, of the Japan Chemical Society.

(iv) Sulfated chitin or chitosan

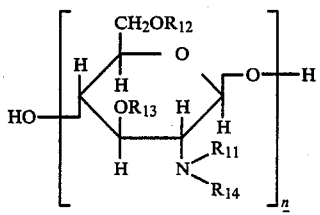  (IV)

wherein $\underline{n}$: >1, preferably 3–100,

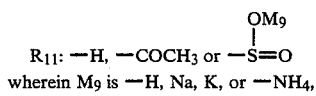

$R_{11}$: —H, —COCH$_3$ or —S(=O)OM$_9$
wherein $M_9$ is —H, Na, K, or —NH$_4$,

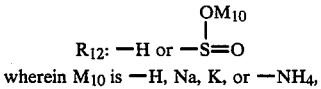

$R_{12}$: —H or —S(=O)OM$_{10}$
wherein $M_{10}$ is —H, Na, K, or —NH$_4$,

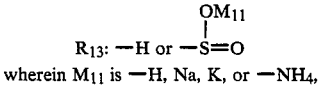

$R_{13}$: —H or —S(=O)OM$_{11}$
wherein $M_{11}$ is —H, Na, K, or —NH$_4$,

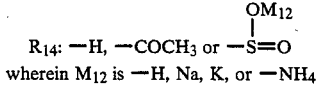

$R_{14}$: —H, —COCH$_3$ or —S(=O)OM$_{12}$
wherein $M_{12}$ is —H, Na, K, or —NH$_4$ $R_{11}$, $R_{12}$, $R_{13}$, and $R_{14}$ may be the same or different, respectively, in each bonded D-glucosamine skeleton.

The sulfated chitin or chitosan can be obtained by reacting an SO$_3$-pyridine complex salt to chitin or chitosan activated in pyridine [see: M. L. Wolfrom et al., The Sulfonation of Chitosan, J. Am. Soc., 81, 1764–1766 (1959)].

(v) N-(glycidyl trimethylammonium) chitosan

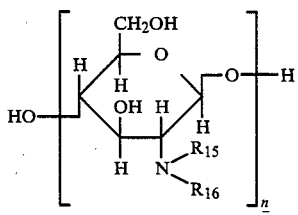  (V)

wherein $\underline{n}$ > 1, preferably 3–100,

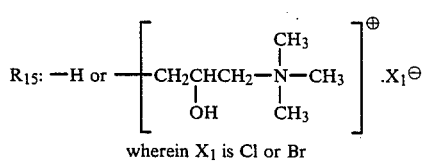

wherein $X_1$ is Cl or Br

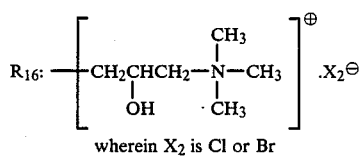

wherein $X_2$ is Cl or Br

The N-(glycidyl trimethylammonium) chitosan can be prepared by addition reacting glycidyl trimethylammonium chloride to chitosan in the presence of a high concentration alkali catalyst at an elevated temperature and pressure.

(vi) Dihydropropyl chitin or chitosan

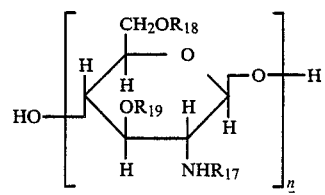  (VI)

wherein $\underline{n}$: >1, preferably 3–100, $R_{17}$: —H or —COCH$_3$,

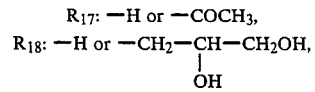

$R_{18}$: —H or —CH$_2$—CH(OH)—CH$_2$OH,

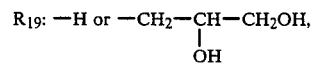

$R_{19}$: —H or —CH$_2$—CH(OH)—CH$_2$OH,

In the above definition, $R_{18}$ and $R_{19}$ are not —H at the same time.

The dihydroxypropyl chitin or chitosan can be prepared by ring-opening and addition reacting epichlorohydrin to alkali chitin or chitosan at the elevated temperature.

(vii) N-(2-hydroxypropyl sulfonic acid) chitosan

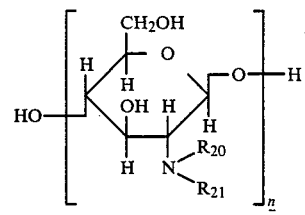  (VII)

wherein $\underline{n}$: >1, preferably 3–100,

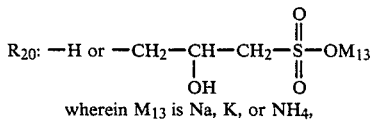

$R_{20}$: —H or —CH$_2$—CH(OH)—CH$_2$—S(=O)$_2$—OM$_{13}$
wherein $M_{13}$ is Na, K, or NH$_4$,

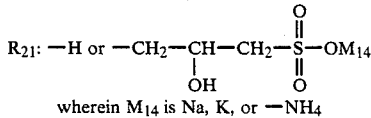

$R_{21}$: —H or —CH$_2$—CH(OH)—CH$_2$—S(=O)$_2$—OM$_{14}$
wherein $M_{14}$ is Na, K, or —NH$_4$ In the above definition, $R_{20}$ and $R_{21}$ are not —H at the same time.

The N-(2-hydroxypropyl sulfonic acid) chitosan can be prepared by addition reacting glycidyl sulfonic acid to chitosan in the presence of an alkali catalyst at an elevated temperature and an elevated pressure.

In the practice of the present invention, chitins and/or chitosans capable of exhibiting buffering capacities in a region of a pH of 5.5 or more are suitably used, whereby the pH in the oral cavity is always maintained at 5.5 or more. Examples of such chitins and chitosans having buffering capacities of a pH of 5.5 or more are preferably powdered chitosan, water-soluble low molecular weight chitosan, ethyleneglycol chitin, phosphorated chitin, and amorphous high molecular weight chitin having an degree of deacetylation of 40 to 60%.

There are no critical limitations to the amount of the chitins and/or chitosans to be formulated into the artificial saliva compositions, although the preferable amount is 0.01% to 5% by weight, more preferably, 0.1% to 2% by weight, based on the total weight of the composition. The use of too large an amount of the chitins and/or chitosans results in too strong buffering capacities, whereas the use of too small an amount of the chitins and/or chitosans results in insufficient buffering capacities.

The artificial saliva composition according to the present invention may optionally contain, in addition to the chitins and/or chitosans, an inorganic component such as potassium chloride, sodium chloride, magnesium chloride, calcium chloride, and potassium phosphated (dibasic), preferably at a concentration of 0.01% to 1% by weight; a germicide or bactericide such as cetyl pyridinium chloride, benzalkonium chloride, benzethonium chloride, and isopropylmethyl phenol, preferably at a concentration of 0.01% to 0.1% by weight; a preservative such as sodium benzoate, methyl p-oxybenzoate, ethyl p-oxybenzoate, and butyl p-oxybenzoate, preferably at a concentration of 0.01% to 0.1% by weight; taste enhancer such as saccharin, 1-menthol, sodium glutamate, and sodium inosinate, preferably at a concentration of 0.01% to 1% by weight; and the like. Furthermore, when the chitins and/or chitosans having a low molecular weight are used, a thickening agent such as polyethylene glycol, propylene glycol, and sorbitol is included, preferably at a concentration of 0.01% to 5% by weight. The thickening agent is not specifically necessary when the chitins and/or chitosans having a high molecular weight are used.

The artificial saliva compositions according to the present invention can be produced in any conventional manner. For example, when the artificial saliva composition is intended to be directly applied to the mouth, the given components are dissolved or suspended in water. Note, when the composition is to be dissolved or suspended in water, the mixture of the given components is formed in an appropriate shape (e.g., powders, tablets, granules, liquids, concentrates) by conventional methods.

As mentioned above, since the artificial saliva composition according to the present invention has a pH buffering capacity similar to natural saliva, the occurrence of a pH of less than 5.5 in the oral cavity can be effectively prevented and, therefore, the generation of caries also can be effectively prevented. Furthermore, since the $LD_{50}$ of chitin is more than 5 g/kg, the chitin has a very high safety factor, and the safety factor of the water-soluble derivatives thereof also is high. For example, the $LD_{50}$ of the nitrite decomposed low-molecular weight chitosan is more than 5 g/kg, the $LD_{50}$ of carboxymethyl chitin is more than 1 g/kg, and the $LD_{50}$ of ethyleneglycol chitosan is more than 1 g/kg. The other water-soluble derivatives are also believed to be similarly safe. Therefore, the artificial saliva composition according to the present invention is remarkably effective for preventing thirst caused by diseases such as sialadenitis, and is effective for also preventing the generation of caries in infants.

EXAMPLES

The present invention will now be further illustrated in detail by, but is by no means limited to, the following Examples, wherein "percentages" are all by weight unless otherwise noted.

Example 1

A 0.5 g amount of the chitins and chitosans listed in Table 1, 0.06 g of potassium chloride, 0.0422 g of sodium chloride, 0.026 g of magnesium chloride hexahydrate, 0.0073 g of calcium chloride dihydrate, and 0.0171 g of potassium phosphate (dibasic) were completely dissolved in 40 g of water, except that the water-insoluble (or slightly water-soluble) chitins and chitosans were thoroughly dispersed in the water. The mixture was diluted with water to obtain 50 g of the artificial saliva composition Nos. 1 to 6.

The extent and range of the buffering capacities of resultant artificial saliva composition Nos. 1 to 6 were evaluated by a buffering capacity curve recording apparatus manufactured by Toa Denpa Kogyo K.K. (Japan).

As comparative examples, a composition not containing chitins and chitosans (i.e., blank), and natural saliva, were evaluated in the same manner.

The results are shown in Table 1. The buffering capacity curves of the artificial saliva composition Nos. 3 and 5 and the blank composition are shown in FIG. 1, wherein curves, a, b, and c represent those of the composition Nos. 3 and 5, and the blank composition, respectively.

TABLE 1

| No. | Chitins, Chitosans | Buffering range (pH) | Buffering capacity ($\beta \times 10^3$) |
|---|---|---|---|
| Blank | — | 6–8 | 1.2 |
| 1 | Powdered chitosan (500 mesh under) | 5.5–7.5 | 14.9 |
| 2 | Chlorine decomposed low M.W. chitosan | 6–7 | 11.0 |
| 3 | Nitrite decomposed low M.W. chitosan | 6–7 | 14.4 |
| 4 | Ethyleneglycol chitin | 5.5–6.5 | 6.7 |
| 5 | Phosphated chitin | 6.3–7.3 | 9.7 |
| 6 | Deacetylated (40–60%) chitin | 6–7.2 | 11.0 |
| Natural saliva | — | 6–7 | 7 |

As is clear from the results shown in Table 1 and FIG. 1, the artificial saliva compositions according to the present invention containing chitins and chitosans have an excellent buffering capacity within a pH range of 5.5 or more. Contrary to this, the blank composition not containing chitins and/or chitosans has a only poor buffering capacity at a pH of 5.5 or more.

Example 2

A 50 g amount of the powdered chitosan listed in Table 1 was ground to a fine powder and 6 g of potassium chloride, 4.22 g of sodium chloride, 0.122 g of magnesium chloride, 0.551 g of calcium chloride, and 1.71 g potassium phosphate (dibasic) were added thereto. The mixture was thoroughly mixed to prepare an oral saliva composition in the form of a powder.

Example 3

An artificial saliva composition in the form of granules was prepared from the components used in Example 2, except that 50 g of the chlorine decomposed low-molecular weight chitosan listed in Table 1 was used instead of 50 g of the powdered chitosans.

The mixture was granulated by adding an appropriate amount of water, followed by drying.

Example 4

An artificial saliva composition in the form of tablets was prepared from the components used in Example 2, except that 50 g of the nitrite decomposed low-molecular weight chitosan listed in Table 1 was used instead of 50 g of the powdered chitosan. To the mixture, 1 g of crystalline cellulose (i.e., Avisel ®) was further added. A 1 g amount of each of the resultant mixtures was compressed into tablet form to prepare the desired tablets.

Example 5

An artificial saliva composition in the form of a liquid was prepared from the components used in Example 2, except that 50 g of the ethyleneglycol chitin listed in Table 1 was used instead of 50 g of the powdered chitosan. The resultant mixture was dissolved in water so that the concentration of the ethylene glycol chitin was 1%. Thus, the desired artificial saliva composition in the form of a liquid was prepared.

Example 6

An artificial saliva composition in the form of a liquid was prepared from the components used in Example 2, except that 50 g of the phosphated chitin listed in Table 1 was used instead of 50 g of the powdered chitosan. The resultant mixture was dissolved in water so that the concentration of the phosphated chitin was 5%. Thus, the desired artificial saliva composition in the form of a liquid was obtained.

Example 7

An artificial saliva composition in the form of powders was prepared from the components used in Example 2, except that 50 g of the deacetylated chitosan having a degree of deacetylation of 40% to 60% listed in Table 1 was used instead of 50 g of the powdered chitosan.

The artificial saliva preparation prepared in Examples 2 to 7 are those which are dissolved or suspended in 100 ml of water when used, having a concentration of the chitins or chitosans of 1%. These compositions were observed to have an excellent buffering capacity within a pH range of 5.5 or more.

We claim:

1. A method of treating hydrodipsia comprising orally administering to a subject suffering from hydrodipsia an artificial saliva composition consisting essentially of at least one buffering compound selected from the group consisting of chitins and chitosans in a medium suitable for an oral composition.

2. A method as claimed in claim 1, wherein said chitins and chitosans provide the composition with a buffering capacity within a region of a pH of 5.5 or more.

3. A method as claimed in claim 1, wherein the concentration of the buffering compound in the composition is 0.01% to 5% by weight.

4. A method of treating hydrodipsia comprising orally administering to a subject suffering from hydrodipsia an artificial saliva composition consisting essentially of at least one buffering compound selected from the group consisting of water-soluble oligomers of chitin and chitosans, water-soluble partially deacetylated chitins, organic and inorganic salts of chitin and chitosan and water-soluble derivatives of chitin and chitosan having a hydrophilic group in a medium suitable for an oral composition.

5. A method as claimed in claim 4, wherein the water-soluble derivatives od chitin and chitosan are polyoxyethylene polyoxpropylene chitins and chitosans, carboxymethyl chitins and chitosans, phosphorated chitin and chitosans, sulfated chitin and chitosan, N-glycidyl trimethylammonium chitosan, dihydropropyl chitin and chitosan, and N-2-hydroxypropyl sulfonic acid chitosan.

* * * * *